US012491095B2

(12) United States Patent
Myung et al.

(10) Patent No.: US 12,491,095 B2
(45) Date of Patent: Dec. 9, 2025

(54) BILIARY STENT HAVING WINDING AND FIXING MEMBER AROUND WHICH PULLING STRING IS WOUND

(71) Applicant: BCM CO., LTD, Gyeonggi-do (KR)

(72) Inventors: Byung Cheol Myung, Gyeonggi-do (KR); Fotheringham Timothy, Greater London (GB); Houn Sung Kim, Gyeonggi-do (KR)

(73) Assignee: BCM CO., LTD, Gyeonggi-do (KR)

(*) Notice: Subject to any disclaimer, the term of this patent is extended or adjusted under 35 U.S.C. 154(b) by 404 days.

(21) Appl. No.: 17/768,384

(22) PCT Filed: Jul. 28, 2020

(86) PCT No.: PCT/KR2020/009790
§ 371 (c)(1),
(2) Date: Apr. 12, 2022

(87) PCT Pub. No.: WO2022/010021
PCT Pub. Date: Jan. 13, 2022

(65) Prior Publication Data

US 2024/0122730 A1 Apr. 18, 2024

(30) Foreign Application Priority Data

Jul. 8, 2020 (KR) ........................ 10-2020-0084242

(51) Int. Cl.
*A61F 2/86* (2013.01)
*A61F 2/04* (2013.01)

(52) U.S. Cl.
CPC .......... *A61F 2/86* (2013.01); *A61F 2002/041* (2013.01); *A61F 2210/0014* (2013.01);
(Continued)

(58) Field of Classification Search
CPC ................ A61F 2002/9511; A61F 2/86; A61F 2250/001; A61F 2002/9528;
(Continued)

(56) References Cited

U.S. PATENT DOCUMENTS

| | | | |
|---|---|---|---|
| 6,132,471 A | 10/2000 | Johlin, Jr. | |
| 9,592,110 B1 | 3/2017 | Dan et al. | |
| 2018/0071099 A1* | 3/2018 | Alon | A61F 2/2412 623/2.11 |

FOREIGN PATENT DOCUMENTS

| | | |
|---|---|---|
| JP | 3602544 B2 | 12/2004 |
| KR | 10-1065365 B1 | 9/2011 |

(Continued)

*Primary Examiner* — Brian E Pellegrino
(74) *Attorney, Agent, or Firm* — IP & T GROUP LLP

(57) ABSTRACT

Disclosed is a biliary stent having a winding and fixing member around which a pulling string is wound, and the biliary stent includes a stent having a cylindrical body having space parts and bent ends formed on both ends thereof and configured such that the pulling string is woven with the space parts in zigzags into a circular band, a knot part is formed firmly so as not to be easily loosened, and a medical procedure is performed to expose the pulling string to an outside of a human body so as to prevent the cylindrical body from slipping inside a biliary tract; the winding and fixing member having a main body including an adhesive part so as to be adhered and fixed to a skin surface; and a cover gauze member configured to cover an entirety of the winding and fixing member and the skin surface.

10 Claims, 11 Drawing Sheets

(52) U.S. Cl.
CPC ................. *A61F 2210/0076* (2013.01); *A61F 2220/0008* (2013.01); *A61F 2220/0075* (2013.01); *A61F 2230/0069* (2013.01); *A61F 2250/0067* (2013.01)

(58) Field of Classification Search
CPC .................. A61F 2250/007; A61F 2/24; A61F 2002/041; A61M 2039/0291; A61M 39/02; A61B 17/0401
See application file for complete search history.

(56) References Cited

FOREIGN PATENT DOCUMENTS

| | | | |
|---|---|---|---|
| KR | 10-2019-0132462 | A | 11/2019 |
| KR | 10-2365507 | B1 | 2/2022 |
| WO | 1998/030173 | A1 | 7/1998 |

* cited by examiner

BILIARY STENT HAVING WINDING AND FIXING MEMBER AROUND WHICH PULLING STRING IS WOUND

This application is a national stage application of PCT/KR2020/009790 filed on Jul. 28, 2020, which claims priority of Korean patent application number 10-2020-0084242 filed on Jul. 8, 2020. The disclosure of each of the foregoing applications is incorporated herein by reference in its entirety.

TECHNICAL FIELD

The present invention relates to a biliary stent having a winding and fixing member around which a pulling string is wound, and more particularly to a biliary stent having a winding and fixing member around which a pulling string is wound, and configured to allow a stent to pass through the skin and the liver of the human body so as to be inserted into a biliary tract at which a lesion occurs, and then to allow the winding fixing member around which the pulling string connected to and extending from the stent installed in the biliary tract and exposed to the outside of the human body is wound to be covered on and fixed to the skin surface, so that contamination of the pulling string, caused by an external environment, is prevented and the stent is prevented from moving in the biliary tract and escaping from the inside of the biliary tract.

BACKGROUND ART

As technology related to a biliary stent having a winding and fixing member around which a pulling string is wound;

a biliary stents is disclosed in Korean Patent Registration No. 10-1065365 (registered on Sep. 8, 2011), and the above biliary stent is inserted into a human body internal organ, as shown in FIG. 10, and is characterized in that a stent 110 having a cylindrical body 114 having space parts 112 formed by weaving or crossing one or more strands of shape memory alloy wires 111 in zigzags and a plurality of bent ends 113 formed on both ends of the cylindrical body 114 along the circumference thereof is formed, both ends of a pulling string 120 woven with the space parts 112 of the cylindrical body 114 in zigzags are tied to be formed into a circular band so as to form a long hanger loop 121 exposed to the outside of the human body so that the stent 110 does not slip within the biliary tract and, the stent 10 is withdrawn and thus easily removed while the circumference of the end of the stent 10 contracts toward the center thereof when the hanger loop 121 is pulled from the outside of the human body during the removal procedure of the stent 110, and the hanger loop 121 of the pulling string 120 passes through the inside of a tube-type port catheter 130 inserted into a part of the human body in which a medical procedure with the stent 110 is performed, extends from one end of the port catheter 131, and is fixed to a port body 32 of a port chamber 130 located outside the human body 32 so that the hanger loop 121 is located inside the port catheter 131 and thus contamination of the hanger loop 121 is prevented.

The above-described biliary stent includes the port catheter 131 installed such that the pulling string 120 connected to the stent 110 is inserted thereinto and thus passes through the skin and the biliary tract of the human body after a medical procedure of inserting the stent 110 into the biliary tract in which a lesion occur so as to allow one end of the port catheter 131 to be exposed to the outside of the human body, and the port body 132 installed at the part of the port catheter 131 exposed to the outside of the human body and connected to the pulling string 120, the medical procedure with the biliary stent is performed such that the stent 110 is installed in the biliary tract and the port catheter 131 passes through the skin and the biliary tract of the human body and is then located inside the human body of a patient, and thus, the port catheter 131 inserted into the skin surface of the human body of the patient provides problems, such as feeling of irritation and inconvenience, to the patient when the patient moves, and pain.

Further, the port catheter 131 moves within the human body due to bending of or damage to the port catheter 131 caused by violent movement of the patient and thus the damaged port catheter 131 may cause inflammation in the human body part into which the port catheter 131 is inserted, or the port catheter 131 escapes from the human body due to violent movement of the patient and thus the stent 110 connected to the port catheter 131 may be removed from the biliary tract and thus the medical procedure of inserting the stent 110 into the biliary trac may be reperformed.

In addition, a plurality of steps of the procedure, such as a step using a catheter (not shown) for inserting the stent into the biliary tract and a step using the port catheter 131, is performed, and this increases patient's fear concerning the medical procedure and provides stress about the medical procedure using the stent and many difficulties to a medical operator who performs the medical procedure of inserting the stent 110 into the biliary tract.

Moreover, as shown in FIG. 11, the stent 110 is inserted into the biliary tract by installing the pulling string 120 having both ends crossing each other at the bent end 113 formed at one end of the stent 110 located in the direction opposite to the insertion direction of the stent 110 and forming a knot part 130 at the pulling string 120 directly adjacent to the bent end 130 and, in order to allow the stent 110 to be inserted into the biliary tract in which a lesion occurs and to become settled in place within the biliary tract, the stent 110 contracted at the time of the procedure is expanded. When the contracted stent 110 expanded, the inner diameter of the bent end 113 formed at the end of the stent 110 located in the direction opposite to the insertion direction of the stent 110 may not be expanded due to contact of the knot part 120 with the bent end, and may thus cause many problems, such as reperformance of the medical procedure of inserting the stent 110 into the biliary tract.

RELATED ART DOCUMENT

Patent Document

Korean Patent Registration No. 10-1065365 (registered on Sep. 8, 2011)

DISCLOSURE

Technical Problem

Therefore, the present invention has been made in view of the above problems, and it is an object of the present invention to provide a new biliary stent having a winding and fixing member around which a pulling string is wound, the biliary stent configured such that the pulling string having a knot part made strongly and firmly and thus fixed so as not to be easily loosened by weaving the pulling string with the bent end of a stent, installed in the biliary tract by passing through the skin and the liver using a catheter, in zigzags is exposed to the outside of the human body, is wound on the winding and fixing member, and is adhered to the skin surface of the human body through the winding and fixing member, the winding and fixing member is fixed to the skin surface of the human body using a cover gauze member, and thereby, prevents a patient from suffering from feeling of irritation and pain due to a port passing through the skin and connected to the biliary tract when the patient body moves for a long time during a medical procedure of inserting the stent into the biliary tract using a conventional port insertion method, allows a patient to experience no feeling of irritation of the stent and the pulling string and thus to be always maintain stability and comfort, and prevents the stent from moving within the biliary tract and escaping from the inside of the biliary tract even if the patient moves a lot.

Further, it is another object of the present invention to provide a new biliary stent having a winding and fixing member around which a pulling string is wound, the biliary stent configured such that the diameter of a stent is easily contracted and expanded due to a designated distance between the bent end of the stent and a knot part formed at the pulling string connected to the bent end, and the inner diameter of the bent end woven with the pulling string is easily expanded due to the designated distance and thus the contracted stent is easily expanded within the biliary tract when the contracted stent is inserted into the biliary tract and is expanded in the biliary tract, so as to overcome a problem in that the inner diameter of the bent end of a conventional stent is not properly expanded due to a knot part formed at a pulling string woven with the bent end of the stent directly adjacent to the bent end, when the contracted stent is expanded within the biliary tract during a medical procedure of inserting the stent into the biliary tract, and thus the medical procedure of inserting the stent into the biliary tract needs to be reperformed.

In addition, it is yet another object of the present invention to provide a new biliary stent having a winding and fixing member around which a pulling string is wound, the biliary stent configured such that the pulling string connected to a stent inserted into the biliary tract is exposed to the outside of the human body, is wound on the winding and fixing member, and is adhered to the skin surface of the human body, and the winding and fixing member is fixed to the skin surface of the human body using a cover gauze member so as to fundamentally prevent the exposed pulling string from being contaminated by an external environment.

Technical Solution

In accordance with the present invention, the above and other objects can be accomplished by the provision of a biliary stent having a winding and fixing member around which a pulling string is wound, the biliary stent including a stent having a cylindrical body having space parts formed by weaving a plurality of shape memory alloy wires with each other in zigzags, and having a plurality of bent ends formed on both ends thereof along the circumference thereof, and configured such that the pulling string is installed so as to be woven with the space parts in zigzags into a circular band, a knot part is formed firmly so as not to be easily loosened and thus to maintain a firmly fixed state thereof by binding both ends of the pulling string, a medical procedure is performed to expose the pulling string to an outside of a human body due to a long length thereof so as to prevent the cylindrical body from slipping inside a biliary tract, one bent end and the knot part are spaced apart from each other by a distance sufficient to allow the cylindrical body to be smoothly contracted and expanded, the distance from the bent end to the knot part is decreased or increased depending on a diameter of the cylindrical body, and the cylindrical body is withdrawn while a circumference of the end thereof contracts toward a center thereof when the knot part is pulled from an outside of the human body during a medical procedure of removing the cylindrical body, the winding and fixing member having a main body including an adhesive part so as to be adhered and fixed to a skin surface of the human body, and configured such that the pulling string is wound on an outer circumference of the main body, and a cover gauze member configured to cover an entirety of the winding and fixing member and the skin surface of the human body adjacent to the winding and fixing member, and adhered and fixed to the skin surface, in order to prevent the winding and fixing member from moving after the winding and fixing member is adhered and fixed to the skin surface.

Further, the knot part may be installed to be spaced apart from the bent end with which the pulling string 15 is woven by a designated distance.

Further, the designated distance may be 3 mm-10 mm.

Further, an outer circumferential surface of the pulling string may be coated with an antibacterial agent.

Further, the pulling string may include a single yarn.

Further, the knot part may include a loop part provided such that one end of the pulling string sequentially passing through the space parts formed at the bent end in zigzags and a remaining end of the pulling string not passing through the space parts comes into contact with each other by a designated length, and a binding part configured such that, after a circular part is formed by bending a front end of the loop part into a circle, the front end of the loop part passes by one end of an upper portion of the circular part, and then passes through the circular part from a lower portion thereof to an upper portion thereof so as to be exposed from a lower surface of the circular part.

Further, the pulling string may be formed of nylon.

Further, the adhesive part may include a double-sided tape.

Further, the main body of the winding and fixing member is configured such that side walls are installed at both sides of the main body by a predetermined distance, and a winding rod is installed and fixed between the side walls.

Further, the winding and fixing member around which the pulling string extending from the stent to a long length to be exposed to the outside of the human body and having the knot part is wound may be inserted into an incision part formed by incising a subcutaneous layer of the skin surface of the human body, the incision part is sutured using a suture thread, and the cover gauze member may be provided to be adhered and fixed to the skin surface while covering all of the incision part and parts adjacent thereto.

Advantageous Effects

A biliary stent having a winding and fixing member around which a pulling string is wound according to the present invention is provided such that the pulling string having a knot part made strongly and firmly and thus fixed so as not to be easily loosened by weaving the pulling string with the bent end of a stent, installed in the biliary tract by passing through the skin and the liver using a catheter, in zigzags is exposed to the outside of the human body, is wound on the winding and fixing member, and is adhered to the skin surface of the human body through the winding and fixing member, the winding and fixing member is fixed to the skin surface of the human body using a cover gauze member, and thereby, prevents a patient from suffering from feeling of irritation and pain due to a port passing through the skin and connected to the biliary tract when the patient body moves for a long time during a medical procedure of inserting the stent into the biliary tract using a conventional port insertion method, allows a patient to experience no feeling of irritation of the stent and the pulling string and thus to be always maintain stability and comfort, and prevents the stent from moving within the biliary tract and escaping from the inside of the biliary tract even if the patient moves a lot.

Further, the biliary stent according to the present invention is provided such that the diameter of the stent is easily contracted and expanded due to a designated distance between the bent end of the stent and the knot part formed at the pulling string connected to the bent end, and the inner diameter of the bent end woven with the pulling string is easily expanded due to the designated distance and thus the contracted stent is easily expanded within the biliary tract when the contracted stent is inserted into the biliary tract and is expanded in the biliary tract, so as to overcome a problem in that the inner diameter of the bent end of a conventional stent is not properly expanded due to a knot part formed at a pulling string woven with the bent end of the stent directly adjacent to the bent end, when the contracted stent is expanded within the biliary tract during a medical procedure of inserting the stent into the biliary tract, and thus the medical procedure of inserting the stent into the biliary tract needs to be reperformed.

In addition, the biliary stent according to the present invention is provided such that the pulling string connected to the stent inserted into the biliary tract is exposed to the outside of the human body, is wound on the winding and fixing member, and is adhered to the skin surface of the human body, and the winding and fixing member is fixed to the skin surface of the human body using the cover gauze member so as to fundamentally prevent the exposed pulling string from being contaminated by an external environment.

BEST MODE

Figure 1:
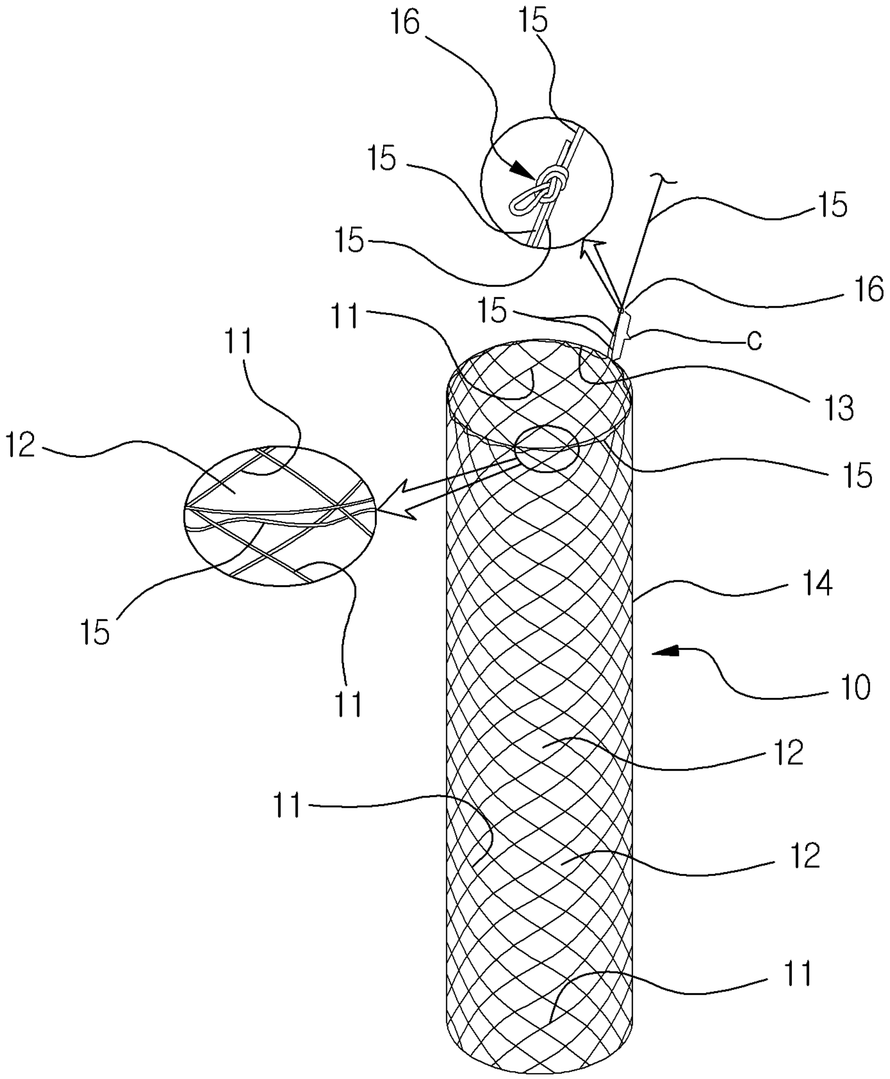
FIG. 1 is a schematic perspective view illustrating bent ends of a stent, a pulling string and a knot part according to the present invention.

Hereinafter, reference will be made in detail to preferred embodiments of the present invention, examples of which are illustrated in the accompanying drawings, to to make the description of the present invention thorough.

The embodiments of the present invention are not limited to the aspects disclosed herein but may be implemented in various different forms. These embodiments are provided for the purpose of describing in more detail to those skilled in the art.

Therefore, the shapes or the like of elements in the drawings may be exaggerated so as to more clearly explain the present invention. The same elements in the respective drawings may be indicated by the same reference numerals or symbols.

Figure 2:
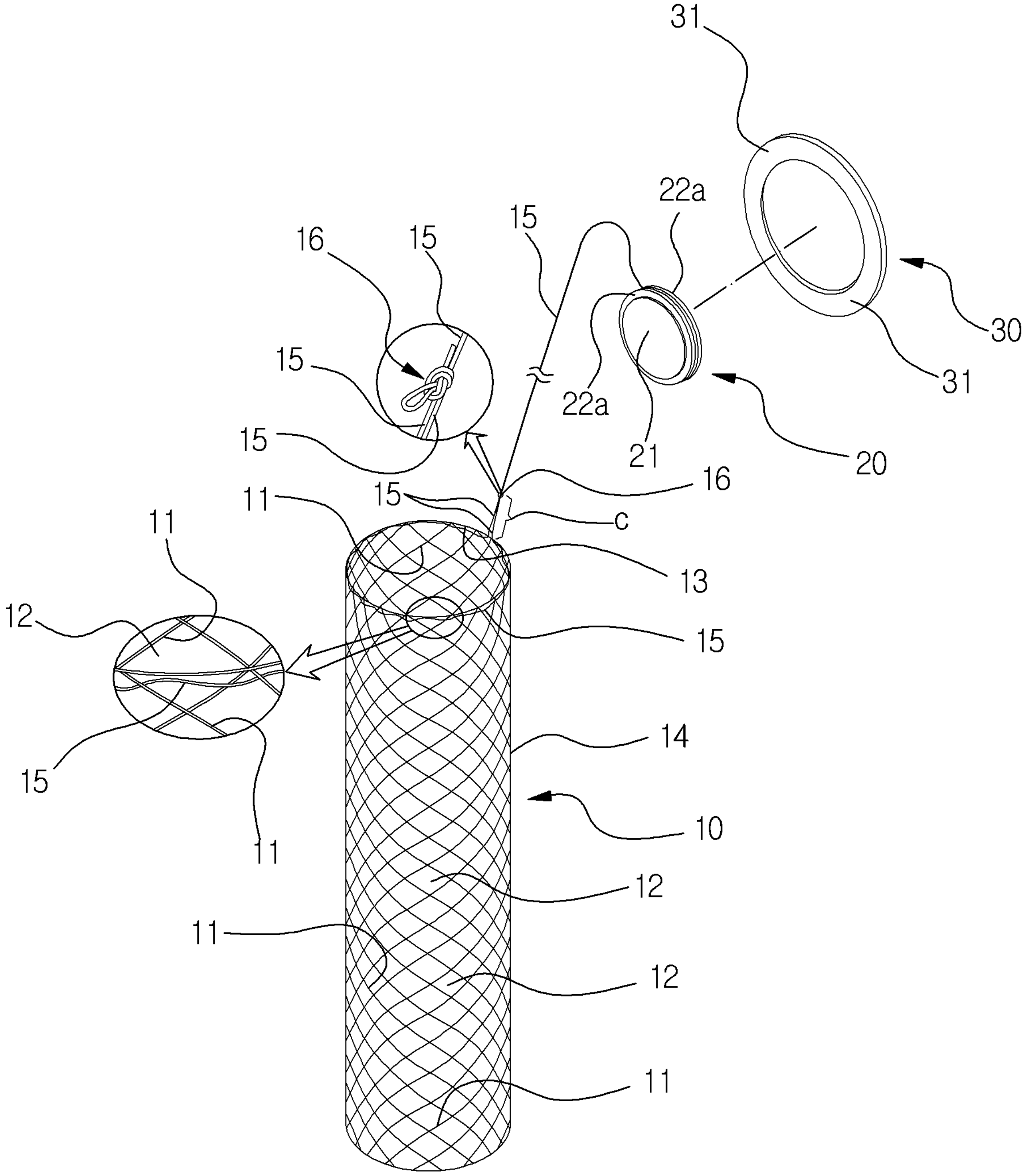
FIG. 2 is an exploded perspective view illustrating the stent, the pulling string, a winding and fixing member and a cover gauze member according to the present invention.
Figure 3:
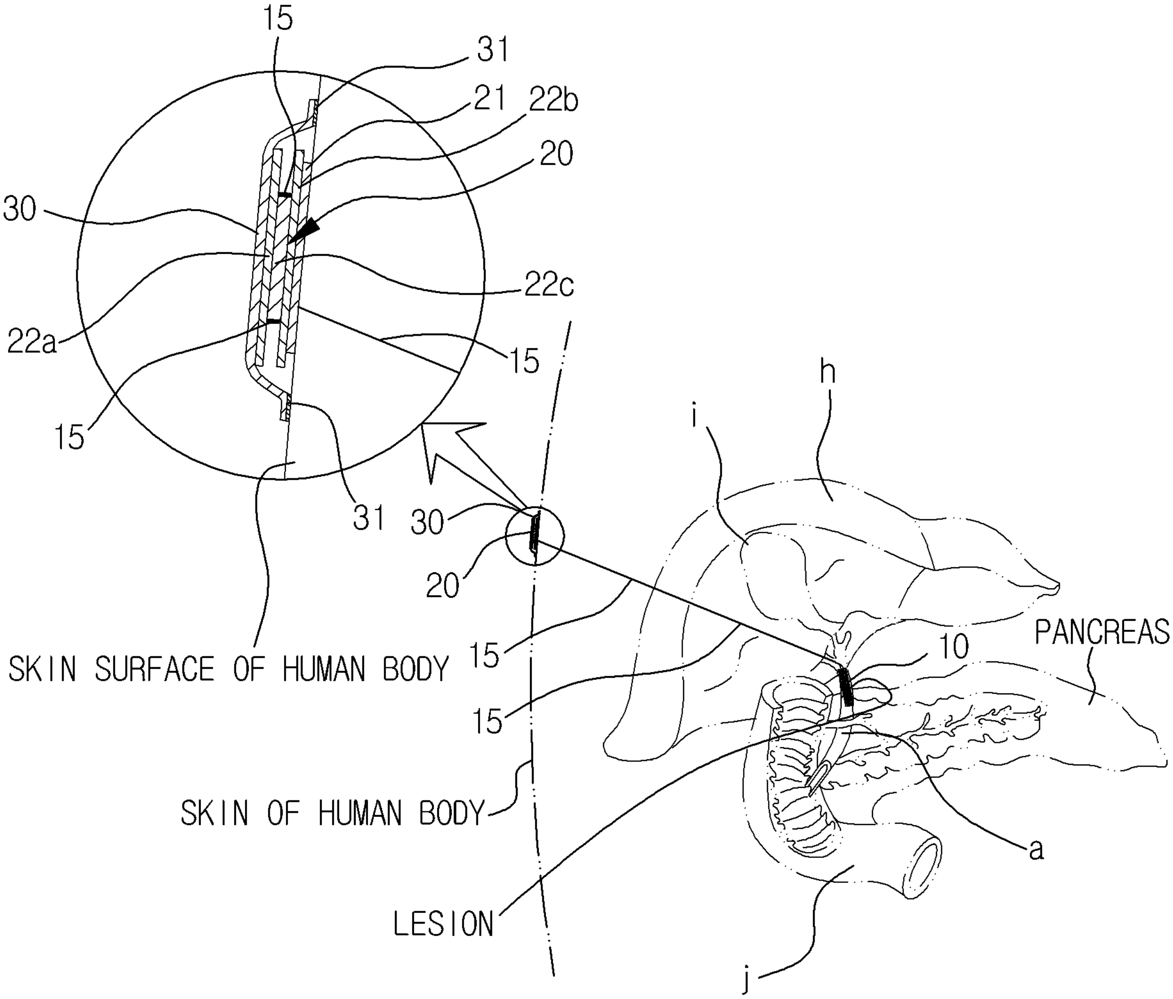
FIG. 3 is a view illustrating a first embodiment of the present invention.
Figure 4:
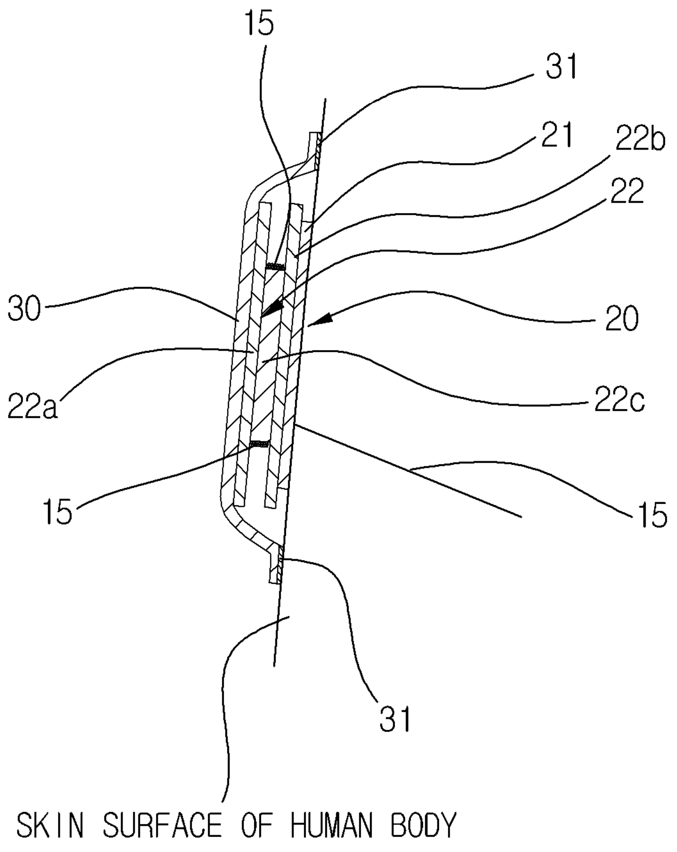
FIG. 4 is a schematic view illustrating the winding and fixing member according to the present invention.
Figure 5:
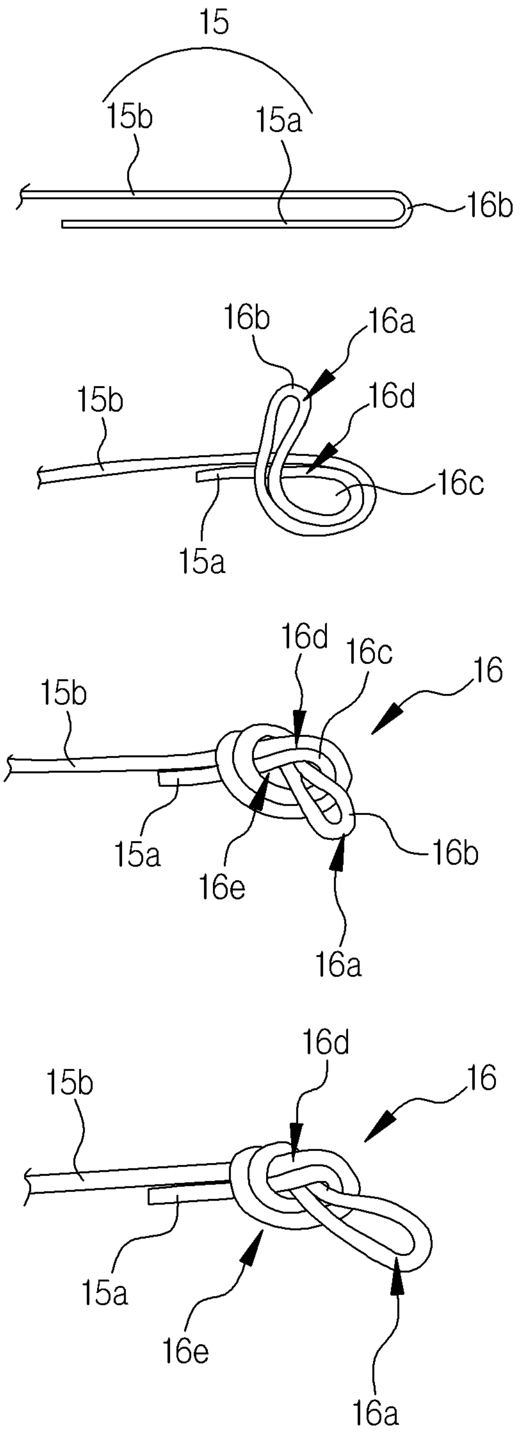
FIG. 5 is a schematic view illustrating a process of tying the knot part according to the present invention.
Figure 6:
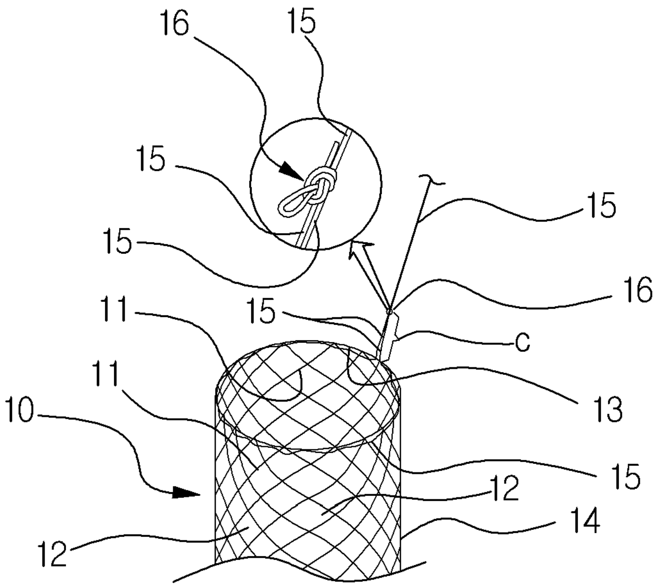
FIG. 6 is a schematic view illustrating a designated distance according to the present invention.
Figure 7:
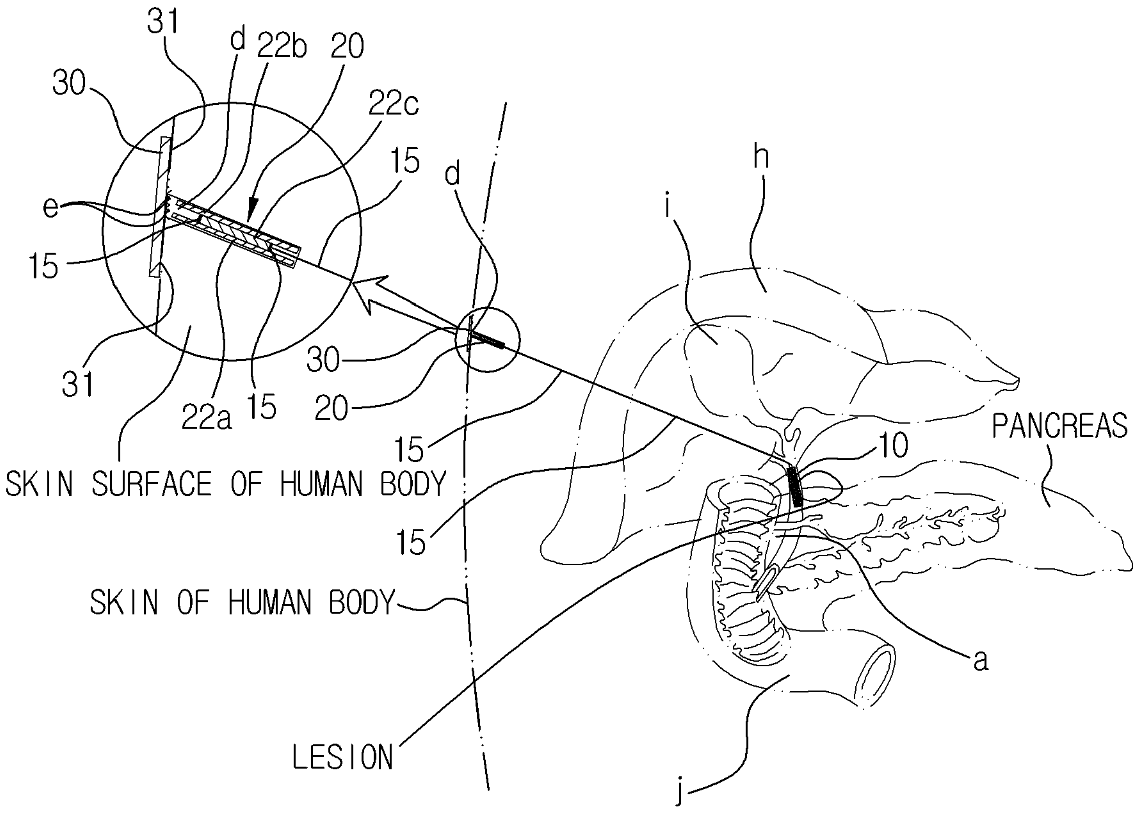
FIG. 7 is a view illustrating a second embodiment of the present invention.
Figure 8:
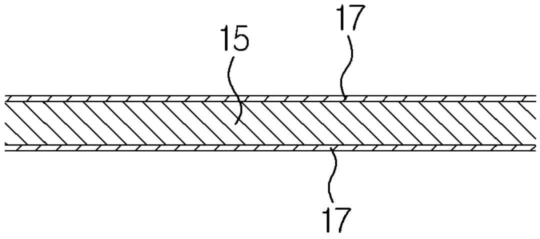
FIG. 8 is a schematic view illustrating an antibacterial layer coated on the pulling string according to the present invention.
Figure 9:
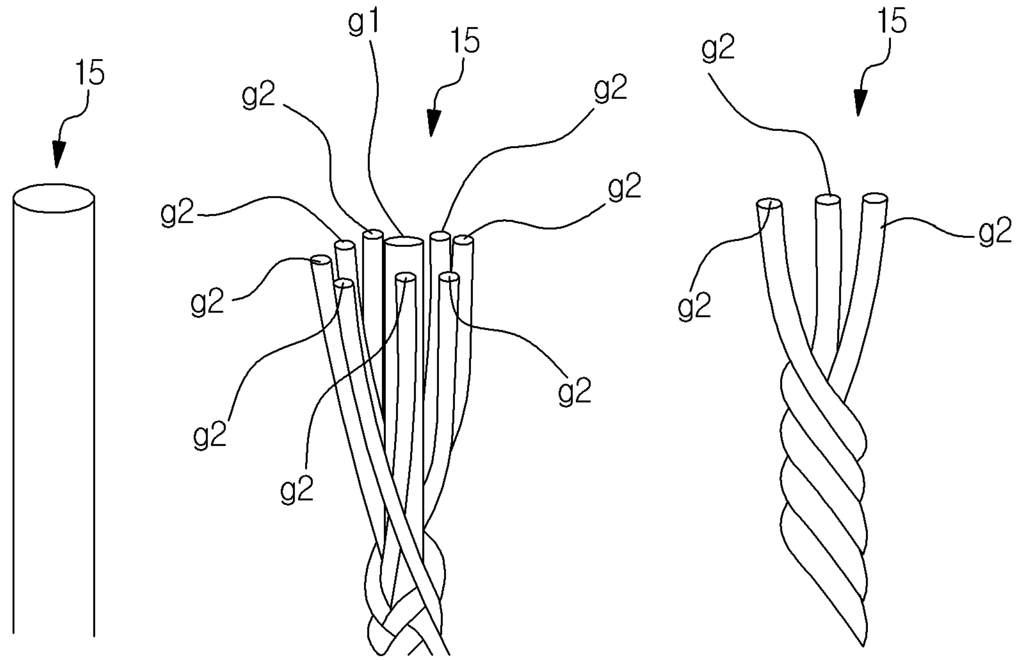
FIG. 9 is an example view illustrating comparison between the pulling string according to the present invention and a conventional pulling string.
Figure 10:
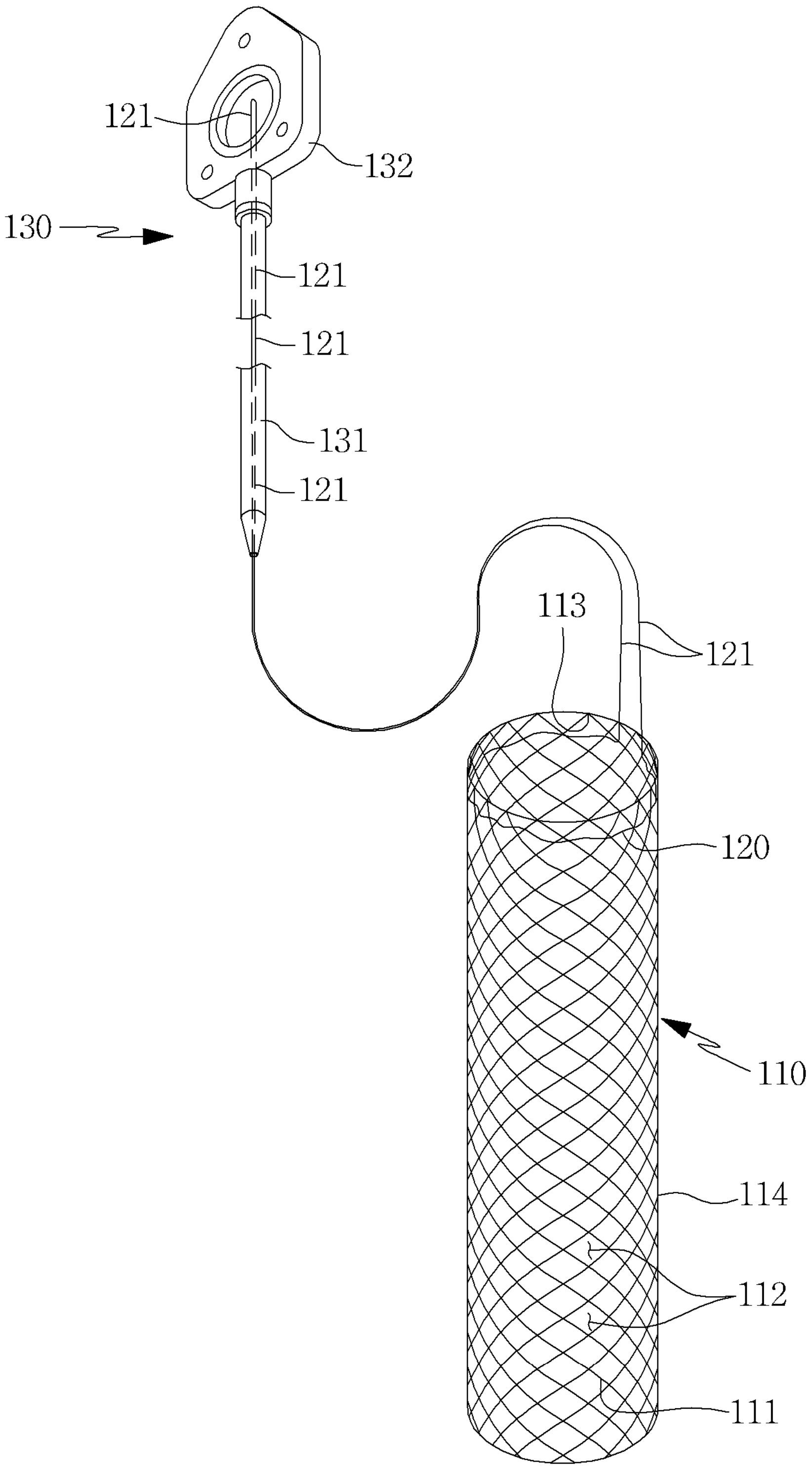
FIGS. 10 and 11 are schematic views illustrating a conventional biliary stent.

FIG. 1 is a schematic perspective view illustrating bent ends of a stent, a pulling string and a knot part according to the present invention, FIG. 2 is an exploded perspective view illustrating the stent, the pulling string, a winding and fixing member and a cover gauze member according to the present invention, FIG. 3 is a view illustrating a first embodiment of the present invention, FIG. 4 is a schematic view illustrating the winding and fixing member according to the present invention, FIG. 5 is a schematic view illustrating a process of tying the knot part according to the present invention, FIG. 6 is a schematic view illustrating a designated distance according to the present invention, FIG. 7 is a view illustrating a second embodiment of the present invention, FIG. 8 is a schematic view illustrating an antibacterial layer coated on the pulling string according to the present invention, and FIG. 9 is an example view illustrating comparison between the pulling string according to the present invention and a conventional pulling string.

A biliary stent having a winding and fixing member around which a pulling string is wound according to the present invention will be described in detail with reference to FIGS. 1 to 9, as follows.

The biliary stent according to the present invention includes a stent 10, the winding and fixing member 20 and a cover gauze member 30.

The stent 10 includes a cylindrical body 14 having space parts 12 formed by weaving or crossing a plurality of shape memory alloy wires 11 each other in zigzags, and having a plurality of bent ends 13 formed at both ends of the cylindrical body 14 along the circumference thereof, as shown in FIGS. 1, 2, 3, 6 and 8.

The stent 10 is formed such that the length and diameter thereof are freely decreased or increased, and is configured such that a medical procedure using the stent 10 may be performed depending on the shape of an organ of the human body.

Further, the pulling string 15 which is sequentially inserted into the space parts 12 in zigzags so as to be woven into a circular band is installed.

Such a pulling string 15 is installed at the bent end 13 formed at one end of the cylindrical body 14 located in the direction opposite to a direction in which the pulling string 15 is inserted into the organ (i.e., in a direction of withdrawing the stent), and both ends of the pulling string 15 are bound together to form a knot part 16.

The knot part 16 is made strongly and firmly so as not to be easily loosened from the pulling string 15 and thus to maintain the firmly fixed state of the knot part 16, and thereby, the knot part 16 is kept in the strongly and firmly fixed state without being loosened in the state in which the knot part 16 is inserted into the human body b for a long period of time of 8 weeks-20 weeks.

The bent end 13 and the knot part 16 are spaced apart from each other by a distance sufficient to allow the cylindrical body 14 to be contracted and expanded without interfering with the knot part 16.

That is, the distance from the bent end 13 to the knot part 16 may have a length sufficient to allow both bent ends 13 of the stent 10 having the cylindrical body 14 to be smoothly contracted (shrunk) and expanded (extended).

The distance from the bent end 13 to the knot part 16 is decreased or increased depending on the diameter of the cylindrical body 14.

That is, the distance from the bent end 13 to the knot part 16 is decreased or increased depending on the diameter of the stent 10 having the cylindrical body 14.

As shown in FIG. 6, the knot part 16 is configured to be spaced apart from the bent end 13 formed at the end of the cylindrical body 14 located in the direction opposite to the direction in which the stent is inserted into the organ (i.e., in the direction of withdrawing the stent) by a designated distance c.

That is, the knot part 16 is configured to be spaced apart from the bent end 13 to which the pulling string 15 is tied by the designated distance c.

Further, the designated distance c may be 3 mm-10 mm, and the value of the designated distance c is not limited so as to facilitate contraction and expansion of the inner diameter of the bent end 13 of the stent 10.

Therefore, when the designated distance c is equal to or less than 3 mm, the length between the knot part 16 and the bent end 13 is short, and thus, the diameter 10 of the stent 10 having the cylindrical body 14 may not be contracted (shrunk) and expanded (extended).

Further, when the designated distance c is equal to or more than 10 mm, the length between the knot part 16 and the bent end 13 is long, and thus, it may be inconvenient to insert the stent 10 into the catheter (not shown) used to perform the medical procedure using the stent.

As described above, the reason why the knot part 16 is configured to be spaced apart from the bent end 13 to which the pulling string 15 is tied is to easily expand the inner diameter of the bent end 13, to which the pulling string 15 is tied, of the contracted stent 10 due to the designated distance of 3 mm-10 mm when the stent 10 contracted to become settled in place in the biliary tract a is expanded inside the biliary tract a in case that the stent 10 is inserted into the biliary tract a in which a lesion occurs.

Figure 11:
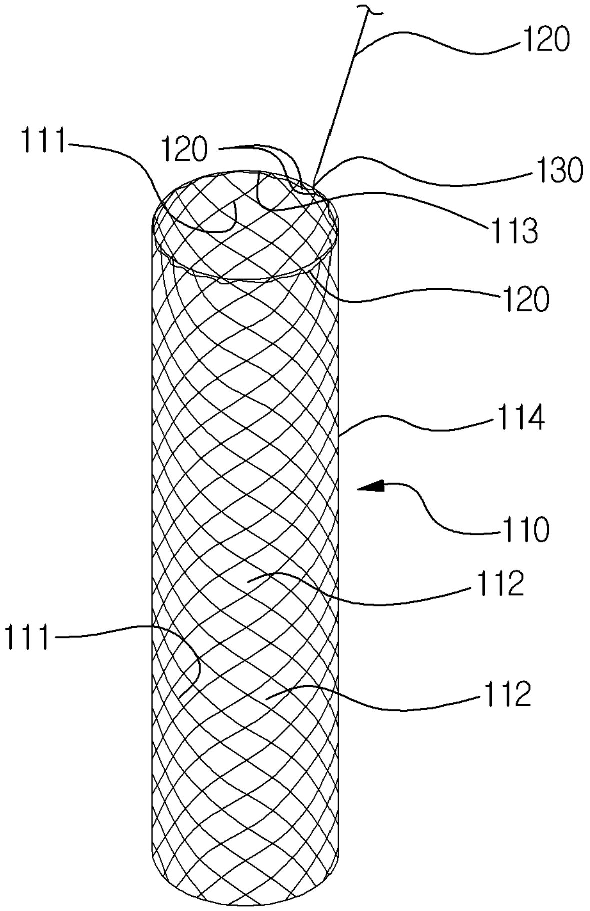

Therefore, as shown in FIG. 11, in case that the conventional stent 110 is inserted into a biliary tract by forming the knot part 120 at the pulling string 120 tied to the bent end 113 of the stent 110 directly adjacent to the bent end 113, when the stent 110 contracted in the biliary tract is expanded within the biliary tract, the inner diameter of the bent end 130 of the stent 110 is not properly expanded due to the knot part 120 formed directly adjacent to the bent end 113 and thus the medical procedure of inserting the stent 110 into the biliary tract a may be reperformed, and thus, the present invention serves to basically prevent such a problem.

Further, since the knot part 16 is configured to be spaced apart from the bent end 13 to which the pulling string 15 is tied by the designated distance c, when the stent 10 is pulled from the outside of the human body b in order to remove the stent 10 from the inside of the biliary tract 8 weeks to 20 weeks after insertion of the stent 10 into the biliary tract a in which the lesion occurs, and thus the stent 10 settled in the expanded state inside the biliary tract a is released from the inside the biliary tract a, the inner diameter of the bent end 13 may be easily tensilely contracted due to the length of the pulling string 15 formed as the designated distance of 3 mm-10 mm provided between the knot part 10 and the bent end 13 of the stent 10 located in the direction opposite to the insertion direction of the stent 10 into the biliary tract a (i.e., in the direction of withdrawing the stent), the stent 10 may be more easily and stably released from the inside of the biliary tract a, and thus, a patient may more stably undergo the removal procedure of the stent 10.

Further, as shown in FIG. 8, the pulling string 15 and the knot part 16 are coated with an antibacterial agent.

That is, an antibacterial layer 17 coated with the antibacterial agent is formed on the outer circumferential surface of the pulling string 15.

The reason why the antibacterial layer 17 coated with the antibacterial agent is formed on the outer circumferential surface of the pulling string 15 is to prevent the pulling string 15 from being contaminated with bacteria when the pulling string 15 is exposed to the outside of the human body b for a long period of time and thus to prevent the medical procedure of inserting the stent 10 into the biliary tract a from being reperformed due to inflammation of the skin of the human body b caused by bacteria contaminating the pulling string 15.

Further, as shown in FIG. 9, the pulling string 15 includes a single yarn.

In addition, the pulling string 15 may be formed of nylon which is a smooth material, but the pulling string 15 is not limited to a specific material.

Therefore, the pulling string 15 including a single yarn formed of nylon is connected to the stent 10 and is thus prevented from being contaminated by bile liquid in the biliary tract a, permeating the pulling string 15 when the pulling string 15 is located in the biliary tract a for 8 weeks to 20 weeks, secures rigidity because the pulling string 15 includes a single yarn, and is more easily released and removed from the skin of the human body b, and on the other hand, the pulling string 15 used in the conventional stent is configured such that a core yarn g1 is installed at the center and a plurality of binding yarns g2 is bound to the outer circumference of the core yarn g1 is configured such that the plurality of binding yarns g2 is woven to cross each other, and is thus contaminated by bile liquid in the biliary tract a, permeating the binding yarns g2 when the pulling string 15 together with the stent 10 is located in the biliary tract a for 8 weeks to 20 weeks, and thereby, the binding yarns g2 are eroded, damaged and then cut.

In order to remove the stent 10 having the pulling string 15 including the binding yarns g2, which are eroded, damaged and then cut, from the inside of the biliary tract a, when the stent 10 is released from the inside of the biliary tract a by pulling the pulling string 15 including the eroded and damaged binding yarns g2, the eroded and damaged pulling string 15 is cut, the stent 10 is not removed from the inside of the biliary tract a, and thus, the removal procedure of the stent 10 from the inside of the biliary tract a is required, and the present invention serves to fundamentally prevent such a removal procedure.

Meanwhile, as shown in FIG. 4, the knot part 16 includes a loop part **16*a* provided such that one end 15*a* of the pulling string 15 sequentially passing through a plurality of space parts 12 formed at the bent end 13 in zigzags and the other end 15***b* of the pulling string 15 not passing through the space parts 12 are in contact with each other by a designated length.

A circular part 16*c* is formed by bending a front end 16*b* of the loop part 16*a* into a circle.

A binding part 16*e* is configured such that, after the circular part 16 is formed, as described above, the front end 16*b* of the loop part 16*a* passes by one end 16*d* of the upper portion of the circular part 16*c*, and then passes through the circular part 16*c* from the lower portion thereof to the upper portion thereof so as to be exposed from the lower surface of the circular part 16*c*.

The reason why the knot part 16 is tied through such a knotting process, as described above, is that the knot part 16 is more easily tied, is configured not to be untied when the knot part 16 is tied once, and is thus stably connected to the stent 10 when the stent 10 is located in the biliary tract a in which the lesion occurs for a long period of time (8 weeks to 20 weeks), and thereby, the stent 10 is more easily removed from the inside of the biliary tract a due to the knot part 16 and the pulling string 15 when the stent 10 is released from the inside of the biliary tract a.

The stent 10 may be configured such that both ends of the pulling string 15 are tied into the knot part 16, the pulling string 15 is exposed to the outside of the human body to a long length so as to prevent the cylindrical body 14 from slipping within the biliary tract a, and, when the pulling string 15 and the knot 16 are pulled from the outside of the human body during the removal procedure of the cylindrical body 14, the cylindrical body 14 is withdrawn while the circumference of the end of the cylindrical body 14 contracts toward the center thereof.

The winding and fixing member 20 includes a main body 22 provided with an adhesive part 21 adhered and fixed to the skin surface of the human body b, as shown in FIGS. 2 and 4.

The adhesive part 21 may include a double-sided tape.

One surface of the double-sided tape is adhered to the main body 22, and the other surface of the double-sided tape is adhered to the skin surface of the human body b so that the winding and fixing member 20 is stably adhered and fixed to the skin surface of the human body b.

Further, the pulling string 15 is configured to be wound on the outer circumference of the main body 22.

That is, the winding and fixing member 20 is configured such that the pulling string 15 extending from the stent 10 inserted into the biliary tract a and exposed to the outside of the human body b is wound on the winding and fixing member 20, and thus fixes the pulling string 15 to the skin surface of the human body b so as to prevent the pulling string 15 from moving and thus to allow the stent 10 to be stably located inside the biliary tract a, thereby preventing the stent 10 connected to the pulling string 15, which is moving, from escaping from the inside of the biliary tract a.

Further, the pulling string 15 is wound on a winding rod 22*c* installed between both side walls 22*a* and 22*b* of the winding and fixing member 20, and is thus prevented from being contaminated by external contaminants.

In addition, the side walls 22*a* and 22*b* are installed at both sides of the main body 22 of the winding and fixing member 20 by a predetermined distance.

The winding rod 22*c* is installed between the side walls 22*a* and 22*b*, and is thus fixed therebetween.

The adhesive part 21 is installed on any one selected from the two side walls 22*a* and 22*b*, the side wall on which the adhesive part 21 is installed is located on the skin surface of the human body b, and the adhesive part 21 is configured to stably adhere and fix the side wall to the skin surface of the human body b.

Further, the winding rod 22*c* is configured such that the pulling string 15 exposed to the outside of the human body b is fixedly wound thereon, thus preventing the pulling string 15 from moving and being contaminated by external contaminants.

The cover gauze member 30 is configured, as shown in FIGS. 2 and 3, to be adhered and fixed to the skin surface while covering the entirety of the winding and fixing member 20 and the skin surface of the human body b adjacent to the winding and fixing member 20 in order to prevent the winding and fixing member 20 from moving, after the winding and fixing member 20 is adhered and fixed to the skin surface.

In order to allow the cover gauze member 30 to be fixed to the skin surface of the human body b while covering the upper surface and the circumference of the winding and fixing member 20, an adhesive member 31 is installed at the circumferential edge of any one of one surface and the other surface of the cover gauze member 30.

The adhesive member 31 serves to more stably and fixedly adhere the cover gauze member 30 to the skin surface of the human body b.

Further, the adhesive member 31 allows one surface of the cover gauze member 30 to cover the entirety of the winding and fixing member 20 and thus stably fixes the winding and fixing member 20 to the skin surface of the human body b, and thereby, the cover gauze member 30 completely blocks external contaminants so as to fundamentally protect the winding and fixing member 20 and the pulling string 15 from the external contaminants.

That is, the pulling string 15 exposed to the outside of the human body is primarily cut off from external contaminants by the winding and fixing member 20 and is secondarily cut off from the external contaminants by the cover gauze member 30, and thereby, the pulling string 15 is fundamentally prevented from being contaminated by the external contaminants.

According to another embodiment of the present invention, as shown in FIG. 9, the winding and fixing member 20 around which the pulling string 15 extending from the stent 10 to a long length to be exposed to the outside of the human body and having the knot part 16 is wound is inserted into an incision part d formed by incising the subcutaneous layer of the skin surface of the human body b.

The incision part d into which the winding and fixing member 20 is inserted is sutured using a suture thread c so as to be closed.

After the incision part d is sutured using the suture thread c, the cover gauze member 30 is provided to be adhered and fixed to the skin surface while covering all of the incision part d and parts adjacent thereto.

In order to allow the cover gauze member 30 to be adhered and fixed to the skin surface of the human body b while covering the incision part d and the parts adjacent thereto, the adhesive member 31 is installed on the circumferential edge of any one selected from one surface and the other surface of the cover gauze member 30.

Therefore, the adhesive member 31 serves to more stably adhere the cover gauze member 30 to the skin surface of the human body b.

The functions of the present invention will be described as follows.

First, after the pulling string 15 sequentially passes through the space parts 12 formed at the bent end 113 of the stent located in the direction opposite to the direction in which the stent 110 having the cylindrical body 14 including a plurality of shape memory alloy wires 11 is inserted into the biliary tract a, the pulling string 15 is withdrawn from the bent end 13, and both ends of the pulling string 15 are tied together so as to form the knot part 16.

The pulling string 15 having the knot part 16 has a sufficient length to be exposed to the outside of the human body even though the stent 10 is inserted into the human body.

As shown in FIG. 6, a medical procedure using the stent 10 having the pulling string 15 is performed when a lesion occurs in the biliary tract a serving as a passage configured to transfer bile in the liver h and bile in the gall bladder i to the pancreatic duct j.

That is, after a portion of the skin of the human body is incised at the outside of the human body, the stent 10 having the pulling string 15 passes through the liver h using a catheter (not shown), which is a device configured to perform the medical procedure using the stent 10, and is inserted into the biliary tract a so as to expand the lesion of the biliary tract a.

When the stent 10 is inserted into the biliary tract a by the catheter (not shown), the contracted stent 10 is expanded within the biliary tract a and is settled in plate. At this time, the inner diameter of the bent end 13 of the stent 10 located in the direction opposite to the direction in which the stent 10 is inserted into the biliary tract a (i.e., in the direction of withdrawing the stent) is more easily expanded due to the designated distance c of 3 mm-10 mm formed between the bent end 13 of the stent 10 located in the direction opposite to the direction in which the stent 10 is inserted into the biliary tract a (i.e., in the direction of withdrawing the stent) and the knot part 16, the other bent end 13 of the stent 10 located in the direction opposite to the designated distance c is also easily expanded within the biliary tract a, and thus, the stent 10 is stably expanded within the biliary tract a and becomes settled in place.

As described above, after the stent 10 is installed in the biliary tract a, the pulling string 15 connected to the stent 10 is wound on the winding rod 22*c* of the winding and fixing member 20, the adhesive part 21 installed on the side wall of the winding and fixing member 20 is adhered and fixed to the skin surface of the human body b, the cover gauze member 30 comes into contact with the skins surface of the human body b while covering the upper surface and the outer circumference of the winding and fixing member 20, and then the cover gauze member 30 having the adhesive member 31 is stably adhered and fixed to the skin surface of the human body b.

When a medical procedure of removing the stent 10 from the inside of the biliary tract a is performed, the cover gauze member 30 adhered to the skin surface of the human body b is primarily removed from the skin surface, the winding and fixing member 20 adhered to the skin surface of the human body b is secondarily removed from the skin surface, and, when the pulling string 15 is partially unwound from the winding rod 22*c* of the winding and fixing member 20 and is then pulled, the stent 10 connected to the pulling string 15 and inserted into the biliary tract a is released from the biliary tract a and the skin surface of the human body b and is thus removed from the biliary tract a and the skin surface of the human body b.

Here, when the pulling string 15 exposed to the outside of the human body b is pulled, the pulling string 15 having the designated distance c of 3 mm-10 mm formed between the bent end 13 of the stent 10 located in the direction opposite to the direction in which the stent 10 is inserted into the biliary tract a (i.e., in the direction of withdrawing the stent) and the knot part 16 pulls the bent end 13 of the stent 10 located in the direction opposite to the direction in which the stent 10 is inserted into the biliary tract a (i.e., in the direction of withdrawing the stent) so as to contract the inner diameter of the bent end 13, and thus, the stent 10 is more easily released from the inside of the biliary tract a, and thereafter, the stent 10 is easily removed from the skin surface of the human body b to the outside.

Although the preferred embodiments of the present invention have been disclosed for illustrative purposes, those skilled in the art will appreciate that various modifications, additions and substitutions are possible, without departing from the scope and spirit of the invention as disclosed in the accompanying claims. Accordingly, it is to be understood that the present invention described as above is not limited by the aspects described herein and the accompanying drawings.

Therefore, the scope of the present invention is defined not by the detailed description, but by the claims and their equivalents. Further, all variations within the scope of the claims and their equivalents are to be construed as being included in the present disclosure.

DESCRIPTION OF REFERENCE NUMERALS OR SYMBOLS

10: stent
11: wire
12: space part
13: bent end
14: cylindrical body
15: pulling string
15*a*: one end
15*b*: the other end
16: knot part
16*a*: loop part
16*b*: front end
16*c*: circular part
16*d*: one end
16*e*: binding part
20: winding and fixing member
21: adhesive part
22: main body
22*a*, 22*b*: side wall
22*c*: winding rod
30: cover gauze member
a: biliary tract
b: human body
c: designated distance
d: cut part
e: suture thread

The invention claimed is:

1. A biliary stent system for use during a medical procedure, the system comprising:
- a winding and fixing member;
- a pulling string wound around the winding and fixing member;
- a stent having
  - a cylindrical body having space parts comprising a plurality of shape memory alloy wires woven with each other in zigzags, and
  - a plurality of bent ends on both ends of the stent along the circumference thereof;
- the pulling string woven with the space parts in the zigzags of the cylindrical body into a circular band; and a knot part attached to the pulling string, wherein the pulling string has a string length configured to place the knot outside of a human body after the biliary stent is implanted, a first bent end of the plurality of bent ends and the knot part are spaced apart from each other by a distance sufficient to allow the cylindrical body to be contracted and expanded, the distance from the first bent end to the knot part is adjustable depending on a diameter of the cylindrical body, the cylindrical body is configured to be withdrawn while a circumference of the end thereof contracts toward a center thereof when the knot part is pulled during the medical procedure, the winding and fixing member has a main body comprising an adhesive part for adherence to a skin surface of the human body, the pulling string is wound on an outer circumference of the main body, the biliary stent system further comprises a cover gauze member configured to cover an entirety of the winding and fixing member and the skin surface of the human body adjacent to the winding and fixing member, and the cover gauze member is configured to be adhered and fixed to the skin surface to prevent the winding and fixing member from moving relative to the skin surface.

2. The biliary stent system according to claim 1, wherein the knot part is installed to be spaced apart from the first bent end, with which the pulling string is woven, by the distance.

3. The biliary stent system according to claim 2, wherein the distance is 3 mm-10 mm.

4. The biliary stent system according to claim 1, wherein an outer circumferential surface of the pulling string is coated with an antibacterial agent.

5. The biliary stent system according to claim 1, wherein the pulling string comprises a single yarn.

6. The biliary stent system according to claim 1, wherein the knot part comprises a loop part provided such that a) one end of the pulling string sequentially passing through the space parts formed at the first bent end in the zigzags and b) a remaining end of the pulling string not passing through the space parts come into contact with each other, and a binding part configured such that a front end of the loop part passes by one end of an upper portion of a circular part of the loop, and then passes through the circular part from a lower portion thereof to an upper portion thereof so as to be exposed from a lower surface of the circular part.

7. The biliary stent system according to claim 1, wherein the pulling string comprises nylon.

8. The biliary stent system according to claim 1, wherein the adhesive part comprises a double-sided tape.

9. The biliary stent system according to claim 1, wherein the main body of the winding and fixing member is configured such that side walls are installed at both sides of the main body, and a winding rod is installed and fixed between the side walls.

10. The biliary stent system according to claim 1, wherein the pulling string extending from the stent and the knot part is wound onto the winding and fixing member.

* * * * *